United States Patent [19]

Mitamura et al.

[11] Patent Number: 6,057,479
[45] Date of Patent: May 2, 2000

[54] PROCESS FOR PREPARING INDAN DERIVATIVES

[75] Inventors: Shuichi Mitamura, Kanagawa; Yasuhisa Asano, Toyama; Tamejiro Hiyama, Sagamihara; Hiroshi Kajiro, Kawasaki, all of Japan

[73] Assignee: Nippon Steel Chemical Co., Ltd., Tokyo, Japan

[21] Appl. No.: 09/091,229

[22] PCT Filed: Jan. 10, 1997

[86] PCT No.: PCT/JP97/00040

§ 371 Date: Jul. 9, 1998

§ 102(e) Date: Jul. 9, 1998

[87] PCT Pub. No.: WO97/25436

PCT Pub. Date: Jul. 17, 1997

[30] Foreign Application Priority Data

Jan. 12, 1996 [JP] Japan .................................. 8-003668
Jun. 7, 1996 [JP] Japan .................................. 8-146312

[51] Int. Cl.[7] .................................................. C07C 211/42
[52] U.S. Cl. .......................... 564/428; 564/420; 564/422; 564/443
[58] Field of Search .................................... 564/418, 422, 564/420, 428, 443

[56] References Cited

U.S. PATENT DOCUMENTS

| | | | |
|---|---|---|---|
| 2,541,967 | 2/1951 | Kolloff | 549/440 |
| 2,916,490 | 12/1959 | Schenck | 544/174 |
| 4,792,628 | 12/1988 | Oshiro | 564/428 |

FOREIGN PATENT DOCUMENTS

| | | |
|---|---|---|
| 60-142919 | 7/1985 | Japan . |
| 61-060610 | 3/1986 | Japan . |
| 7-228586 | 8/1995 | Japan . |
| 7-242624 | 9/1995 | Japan . |
| WO 9611282 | 4/1996 | WIPO . |
| WO 9636724 | 11/1996 | WIPO . |

OTHER PUBLICATIONS

Tetrahedron Lett. by Ghosh A., "Stereoselective Reduction of alph Hydroxy Oxime Ethers: A Convienent Route to Cis–1,2– Amino Alcohols". vol. 32, No. 6, pp. 711–714, 1991.
CA:124:55593 ab of JP07242614 by Oda Y, Sep. 1995.
CA:77:75331 J. Organometallic Chem 39 (2) pp. 381–387 by Giannotti.C., 1972.
CA:104:124454 Drug Metab. Dispos. 14 (1) pp. 97–101 by Bartels M.J., 1986.

*Primary Examiner*—Gary Geist
*Assistant Examiner*—Jean F Vollano
*Attorney, Agent, or Firm*—Birch, Stewart, Kolasch & Birch, LLP

[57] ABSTRACT

This invention relates to a process for preparing indan derivatives and comprises a process for preparing cis-1-amino-2-indanol by treating (±)indan-1,2-diol and/or its 2-formate derivative with specific microbes to give optically active 2-hydroxy-1-indanone, converting the optically active 2-hydroxy-1-indanone to its oxime, and treating the oxime with hydrogen or a hydrogen donor in the presence of a heterogeneous hydrogenation catalyst, a process for preparing optically active 2-hydroxy-1-indanone and/or optically active indan-1,2-diol by treating (±)indan-1,2-diol and/or its 2-formate derivative with specific microbes, and a process for preparing cis-1-amino-2-indanol by treating the oxime of 2-hydroxy-1-indanone with hydrogen or a hydrogen donor in the presence of a heterogeneous hydrogenation catalyst.

5 Claims, No Drawings

PROCESS FOR PREPARING INDAN DERIVATIVES

This application is the national phase under 35 U.S.C. §371 of prior PCT International Application No. PCT/JP97/00040 which has an International filing date of Jan. 10, 1997 which designated the United States of America, the entire contents of which are hereby incorporated by reference.

FIELD OF TECHNOLOGY

This invention relates to a process for preparing indan derivatives which are useful as synthetic intermediates for pharmaceuticals and the like. In particular, this invention relates to a process for preparing optically active 2-hydroxy-1-indanone from (±)indan-1,2-diol or its 2-formate derivative with the use of microbes and to a process for preparing indan derivatives such as cis-1-amino-2-indanol from 2-hydroxy-1-indanone derivatives.

BACKGROUND TECHNOLOGY

As for the preparation of 2-hydroxy-1-indanone, several processes such as hydrolysis of the corresponding acetate have been known. However, processes directed to the preparation of optically active substances are very few and only the following two processes have been reported. One of them is effected by treating an alkyl-substituted siloxyindene with an oxidizing agent in the presence of an optically active manganese complex catalyst followed by desilylation [Kokai Tokkyo Koho Hei 7-228586 (1995)]. This process, however, necessitates the synthesis of an optically active manganese complex catalyst of complicated molecular structure. The other is effected by oxidizing 1-indanone or 2-indanone with a special enzyme. According to this process, treating 1-indanone with naphthalene deoxygenase gives (R)2-hydroxy-1-indanone, but the product shows a low optical purity of 22%. On the other hand, treating 2-indanone with naphthalene deoxygenase gives (S)2-hydroxy-1-indanone, but none of the (R) for m. The latter process requires a special enzyme and is not applicable to the cases where the target is a substance of (R) form with high optical purity [Reskich, S. M. et al. Appl. Environ. Microbiol., 60, 3323 (1994)].

In consequence, there has been a demand for development of a simple process for preparing optically active 2-hydroxy-1-indanones of high optical purity.

The following processes are known for the preparation of cis-1-amino-2-indanol: indene is subjected to addition reaction with iodine isocyanate (INCO) and then treated with methanol, the resulting β-iodocarbamate is heated to give oxazolidone, and the oxazolidone is hydrolyzed (J. Org. Chem., 1967, 32, 540); indene is converted in two steps to trans-1-amino-2-indanol, which is treated successively with benzoyl chloride and thionyl chloride, and the resulting oxazoline is hydrolyzed (J. Am. Chem. Soc., 1951, 73, 1639 and J. Med. Chem., 1992, 35, 1685); 1-methoxycarbonyl-2-indanone is converted in three steps to β-hydroxylcarbamate, which is converted to oxazolidone and hydrolyzed (Tetrahedron, 1991, 47, 4941); indene is converted to indene oxide, indan-1,2-diol, or 2-bromo-1-indanol and then allowed to react with acetonitrile in the presence of sulfuric acid to give oxazoline, which is hydrolyzed (Tetrahedron Lett., 1995, 36, 3993); 2-hydroxy-1-indanone-o-benzyloxime is reduced with borane in tetrahydrofuran (Tetrahedron Lett., 1991, 32, 711).

Any of these processes, however, requires an increased number of reaction steps and expensive reactants to place the amino and hydroxyl groups in cis configuration and faces a number of problems in its application on a commercial scale.

Moreover, in the cases where indan derivatives such as cis-1-amino-2-indanol and its derivatives are used as synthetic intermediates for pharmaceuticals, they at times need to be optically active. If such is the case, it is advantageous to carry out optical resolution in the earliest possible stage in the course of the preparation because the yield of the object indan derivatives is reduced to approximately ½ during optical resolution.

Accordingly, it is an object of this invention to provide a process being applicable with ease on a commercial scale for first preparing optically active 2-hydroxy-1-indanone with the use of microbes and then preparing optically active cis-1-amino-2-indanol from said optically active 2-hydroxy-1-indanone, the latter process being applicable with ease on a commercial scale.

Another object of this invention is to provide a process for preparing optically active 2-hydroxy-1-indanone with the use of microbes.

A further object of this invention is to provide a process, readily applicable on a commercial scale, for preparing 2-indanol derivatives, in particular, cis-1-amino-2-indanol.

DISCLOSURE OF THE INVENTION

Thus, this invention relates to a process for preparing indan derivatives which comprises treating (±)indan-1,2-diol or its 2-formate derivative with microbes possessing the capability of converting said (±)indan-1,2-diol or its 2-formate derivative to optically active 2-hydroxy-1-indanone to give optically active 2-hydroxy-1-indanone, treating said optically active 2-hydroxy-1-indanone with a compound of the following general formula (4)

$$H_2N-X-R \qquad (4)$$

(wherein X designates —O— or —NH— and R designates hydrogen atom, alkyl group or aryl group) to give a compound of the following general formula (1)

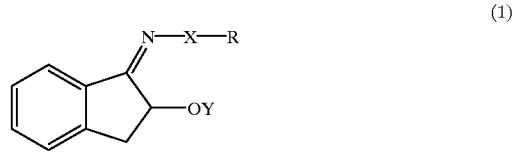

(1)

(wherein X and R are as defined above and Y designates hydrogen atom), and treating said compound of the general formula (1) with hydrogen or a hydrogen donor in the presence of a heterogeneous hydrogenation catalyst to give cis-1-amino-2-indanol represented by the following general formula (2)

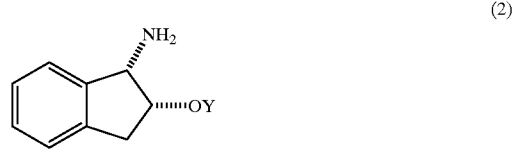

(2)

(wherein Y is hydrogen atom).

This invention also relates to a process for preparing indan derivatives which comprises treating (±)indan-1,2- diol or its 2-formate derivative (a) with microbes possessing the capability of converting said (±)indan-1,2-diol or its 2-formate derivative to optically active 2-hydroxy-1-indanone to give optically active 2-hydroxy-1-indanone (b) and/or optically active indan-1,2-diol (c) as shown by the following reaction (1)

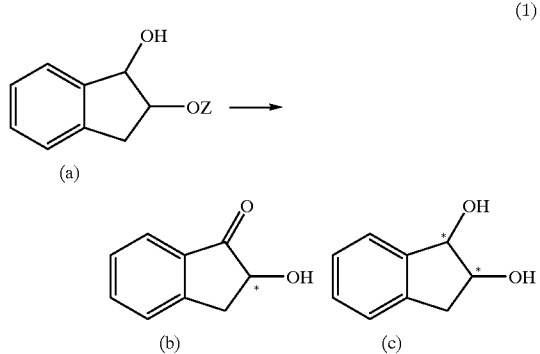

(wherein Z is hydrogen atom or formyl group and * designates the position of the atom of an optically active center).

Microbes useful for the process of this invention include those belonging to the genus of Bacillus, Arthrobacter, Corynebacterium or Pseudomonas.

Here, (±)indan-1,2-diol or its 2-formate derivative (a) may be either cis or trans and it is possible to obtain optically active 2-hydroxy-1-indanone (b) of (R) or (S) form by proper selection of microbes.

The reactions involved here proceed according to the following equations (2) to (5) wherein the symbols are as defined in the reaction (1).

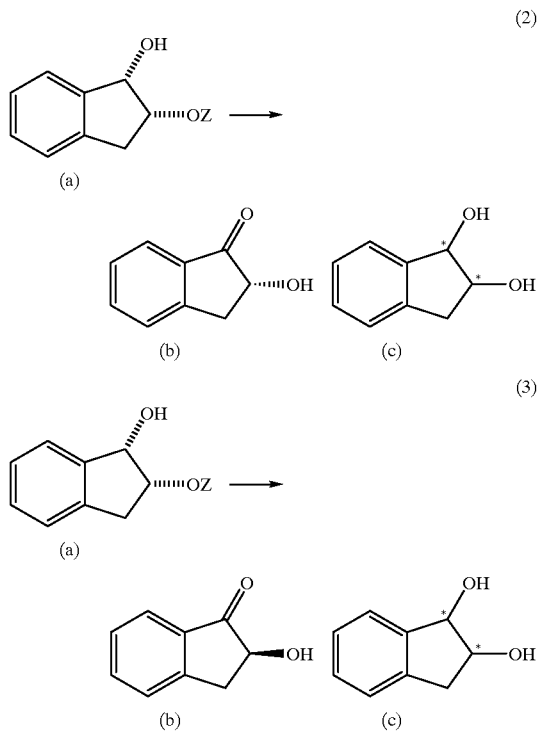

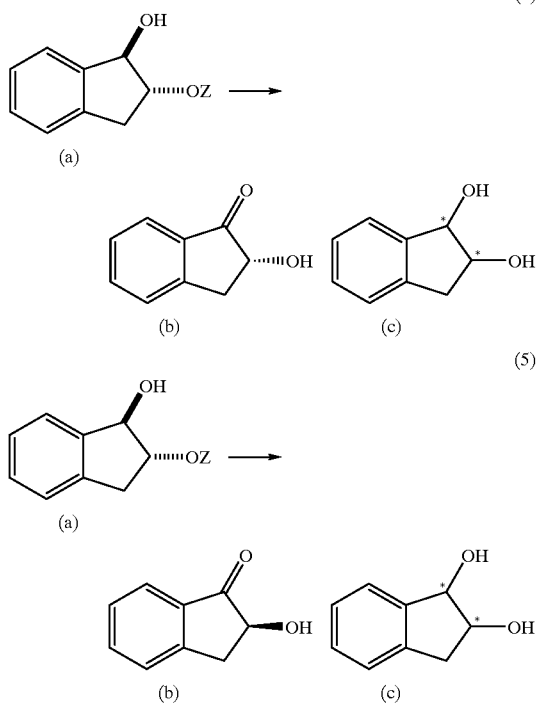

Firstly, the reaction (2) refers to an example in which the starting material (a) is cis and the compound (b) is of (R) form and the microbes suitable for this reaction include those belonging to the genus of Bacillus, Corynebacterium, Arthrobacter or Psudomonas.

Secondly, the reaction (3) refers to an example in which the starting material (a) is cis and the compound (b) is of (S) form and the microbes suitable for this reaction include those belonging to the genus of Arthrobacter or Psudomonas.

Thirdly, the reaction (4) refers to an example in which the starting material (a) is trans and the compound (b) is of (R) form and the microbes suitable for this reaction include those belonging to the genus of Corynebacterium, Arthrobacter or Psudomonas.

Finally, the reaction (5) refers to an example in which the starting material (a) is trans and the compound (b) is of (S) form and the microbes suitable for this reaction include those belonging to the genus of Arthrobacter or Bacillus.

Furthermore, this invention relates to a process for preparing indan derivatives which comprises treating a compound of the following general formula (1)

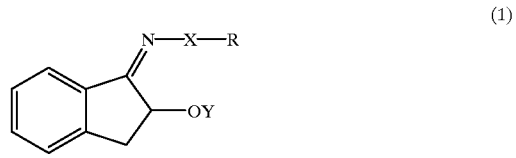

(wherein X is —O— or —NH—, R is hydrogen atom, alkyl group or aryl group and Y is hydrogen atom, acyl group or benzyl group) with hydrogen or a hydrogen donor in the presence of a heterogeneous hydrogenation catalyst to give cis-1-amino-2-indanol or its derivative represented by the following general formula (2)

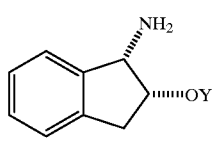

(2)

(wherein Y is hydrogen atom, acyl group or benzyl group).

Concrete examples of those microbes which possess the capability of converting (±)indan-1,2-diol or its 2-formate derivative to optically active 2-hydroxy-1-indanone and/or optically active indan-1,2-diol are *Bacillus cereus* 2HB, *Pseudomonas aeruginosa* IN, Corynebacterium.sp.2HI, Arthrobacter.sp.1HE, and Arthrobacter.sp.1HB.

Although R is hydrogen atom, an alkyl group such as methyl and ethyl, or an aryl group such as phenyl and benzyl in the aforementioned general formula (1), it is preferable that X is oxygen atom and R is hydrogen atom. A heterogeneous hydrogenation catalyst for the hydrogenation of a compound of the general formula (1) is preferably based on nickel, palladium or platinum.

In the aforementioned general formula (2), the notation —$NH_2$ and —OY for the substituents shows that both substituents are pointed either upward or backward from the plane of the paper. The same notation is employed in the reactions (2) to (5) above and —OH and —OZ indicate the same arrangement as in the general formula (2) or the cis configuration while —OH and —OZ indicate that one points upward and the other backward from the plane of the paper or the trans configuration.

This invention will be described in detail below.

(±)cis-Indan-1,2-diol or its 2-formate derivative to be used as starting material (a) in this invention is prepared by treating indene with aqueous hydrogen peroxide in formic acid according to the procedure of Taylor [Taylor, J. E., Synthesis 1142 (1985)]. (±)trans-Indan-1,2-diol is prepared by the procedure described in J. Org. Chem., 37, 3182 (1972).

The microbes to be used in this invention are those strains which were isolated from the natural world by the present inventors and include 2HB, IN, 2HI, 1HE and 1HB.

The mycological properties of these strains are shown in Table 1.

TABLE 1

| Item of observation | 1HB | 1HE | 2HB | 2HI | IN |
|---|---|---|---|---|---|
| a) Morphology | | | | | |
| 1: Cell shape | Coryneform | Coryneform | Long rod | Coryneform | Short rod |
| 2: Polymorphism | Coryneform | Coryneform | nonpolymorphic | Coryneform | nonpolymorphic |
| 3: Motility | Nonmotile | Nonmotile | Nonmotile | Nonmotile | Motile |
| 4: Spore | Absent | Absent | Present | Absent | Absent |
| 5: Gram stain | Positive | Positive | Positive | Positive | Negative |
| 6: Acid-fastness | Non-acid-fast | Non-acid-fast | Non-acid-fast | Non-acid-fast | Non-acid-fast |
| b) Condition of growth on different media | | | | | |
| 1: Plating on nutrient agar (30° C., 7 days) | | | | | |
| i) Diameter of colony (mm) | 1~2.5 | 1~3 | 3~6 | 1~4 | 3~5 |
| ii) Shape of colony | Circular | Circular | Circular | Circular | Circular |
| iii) Surface condition of colony | Smooth | Smooth | Smooth | Smooth | Smooth |
| iv) Protruding condition of colony | Convex | Convex | Projecting | Convex | Protruding |
| v) Margins of colony | Whole | Whole | Whole | Whole | Whole |
| vi) Color of colony | White | Yellow | Creamy | Creamy | Brown |
| vii) Transparency of colony | Translucent | Translucent | Opaque | Translucent | Translucent |
| viii) Gloss of colony | Noticeable | Somewhat noticeable | Noticeable | Noticeable | Noticeable |
| ix) Formation of soluble pigments | Not formed | Not formed | Not formed | Not formed | Formed (brown) |
| 2: Slant culture on nutrient agar (30° C., 7 days) | | | | | |
| i) Condition of growth | Good | Good | Good | Good | Good |
| ii) Gloss of colony | Noticeable | Noticeable | Noticeable | Non-noticeable | Noticeable |
| 3: Liquid culture on nutrient broth | Growth on surface | Growth on surface | Growth throughout | Growth on surface | Growth on surface |
| 4: Nutrient gelatin (liquefaction) (20° C., 30 days) | − | + | + | − | + |
| 5: Litmus milk (30° C., 7 days) | No change | Acid clotting | Lysis | No change | Lysis |
| c) Physiological properties | | | | | |
| 1: Reduction of nitrates | + | + | + | + | + |
| 2: Reduction of nitrites | + | + | + | + | + |
| 3: Denitrification reaction | − | + | + | − | − |
| 4: Methyl red | − | − | − | − | − |
| 5: Voges-Proskauer reaction | − | − | + | − | − |
| 6: Formation of indole | − | − | − | − | − |
| 7: Formation of hydrogen sulfide | − | − | − | − | − |
| 8: Hydrolysis of starch | + | + | − | + | − |
| 9: Utilization of citric acid | | | | | |
| i) Christensen's medium | − | − | + | + | + |

TABLE 1-continued

| Item of observation | 1HB | 1HE | 2HB | 2HI | IN |
|---|---|---|---|---|---|
| ii) Shimmons' medium | − | − | − | − | + |
| iii) kosei's medium | | | + | | |
| 10: Formation of pigment | | | | | |
| i) King A medium | − | − | − | − | fluorescence |
| ii) King B medium | − | − | − | − | fluorescence |
| iii) Pseudomonas F medium | − | − | − | − | fluorescence |
| iv) Pseudomonas P medium | − | − | − | − | fluorescence |
| 11: Urease | − | − | + | − | + |
| 12: Oxidase | + | − | − | − | + |
| 13: Catalase | + | + | + | + | + |
| 14: Range of growth | | | | | |
| i) pH | 6~9 | 6~9 | 5~9 | 5~9 | 5~9 |
| ii) Temperature | 15~45 | 10~45 | 15~55 | 10~45 | 10~45 |
| 15: Behavior toward oxygen | Aerobic | Aerobic | Facultative anaerobic | Aerobic | Aerobic |
| 16: O—F test (glucose) | (Oxidation) | (Oxidation) | No reaction | (Oxidation) | (Oxidation) |
| 17: Phenylalanine deaminase | − | − | − | − | − |
| 18: Lysine decarboxylase | − | − | − | − | + |
| 19: Arginine decarboxylase | − | − | − | − | + |
| 20: Ornithine decarboxylase | − | − | − | − | − |
| 21: Capability of assimilating malonic acid | − | − | − | − | + |
| 22: β-Galactosidase | + | + | + | + | − |
| 23: DNAse | + | − | + | + | + |
| 24: Phosphatase | − | − | − | − | |
| 25: Hydrolysis of esculin | − | + | + | + | − |
| 26: β-Glucosidase | − | + | + | + | |
| 27: Hydrolysis of hippuric acid | + | + | − | + | |
| 28: Hydrolysis of pyroglutamic | − | + | − | − | |
| 29: Leucine aminopeptidase | − | + | − | − | |
| 30: Alkalinization of acetamide | | | | | + |
| 31: Growth at pH 5.7 | | | + | | |
| 32: Egg Yolk reaction | | | + | | |
| 33: Hydrolysis of casein | | | + | | |
| 34: Decomposition of tyrosine | | | + | | |
| 35: pH in V-P medium | | | 5.2 | | |
| 36: Assimilation of saccharides | | | | | |
| i) Glucose | | | | | + |
| ii) Arabinose | | | | | − |
| iii) Mannose | | | | | − |
| iv) Mannitol | | | | | + |
| v) N-Acetylglucosamine | | | | | + |
| vi) Maltose | | | | | − |
| vii) Gluconic acid | | | | | + |
| viii) Caprylic acid | | | | | + |
| ix) Adipic acid | | | | | + |
| x) Maleic acid | | | | | + |
| xi) Citric acid | | | | | + |
| xii) Phenylacetic acid | | | | | − |
| 37: Formation of acids from saccharides | | | | | |
| i) Glucose | + | + | + | + | − |
| ii) Lactose | − | − | − | − | − |
| iii) Saccharose | − | + | − | − | − |
| iv) D-Mannitol | − | − | − | − | − |
| v) Dutcitol | − | − | − | − | − |
| vi) D-Adonitol | − | ± | − | − | − |
| vii) Inositol | − | − | − | − | − |
| viii) D-Sorbitol | − | − | − | − | − |
| ix) L-Arabinose | − | + | − | − | + |
| x) Raffinose | − | − | − | − | − |
| xi) L-Rhamnose | − | − | − | − | − |
| xii) Maltose | − | − | − | − | − |
| xiii) Xylose | − | − | − | − | − |
| xiv) Trehalose | − | − | − | − | − |
| xv) Cellobiose | − | − | − | − | − |
| xvi) Melibiose | − | − | − | − | − |
| xvii) D-Mannose | − | + | − | − | − |
| xviii) Glycerose | − | ± | − | − | − |
| xix) Galactose | − | − | − | − | − |
| xx) Inulin | − | − | − | − | − |
| xxi) Salicin | − | − | − | + | − |
| d) Other properties | | | | | |

TABLE 1-continued

| Item of observation | 1HB | 1HE | 2HB | 2HI | IN |
|---|---|---|---|---|---|
| 1) Vitamin requirement | − | − | − | − | − |
| 2) Halotolerance 5% | + | + | + | + | + |
| Halotolerance 7% |  |  | + |  |  |
| Halotolerance 10% | − | + | − | − | − |
| Halotolerance 15% | − | + | − | − | − |
| e) Analysis of cell wall |  |  |  |  |  |
| 1) Presence of mycolic acids | − | − |  | + |  |
| 2) Kind of amino acid | Lysine | Lysine |  | neso-DAP |  |
| 3) Kind of fatty acid | Iso/anti Isobranched acid Arthrobacter sp. | Iso/anti Isobranched acid Arthrobacter sp. | Bacillus cereus | Hexadecanoic acid Octadecanoic acid Corynebacteriun sp. | Pseudomonas aeruginosa |

On the basis of the aforementioned mycological properties, each of the se strains was identified as follows.

Strain 2HB is a gram-positive spore-forming long rod and was identified as *Bacillus cereus* for its positive Voges-Proskauer test and positive yolk reaction. Furthermore, this strain was considered a new strain of *Bacillus cereus* because of its capability of converting (±) indan-1,2-diol to optically active 2-hydroxy-1-indanone and identified as *Bacillus cereus* 2HB.

Strain IN is a motile gram-negative fluorescent pigment-producing short rod and was identified as *Pseudomonas aeruginosa* as it grows at 45° C. This strain was considered a new strain of *Pseudomonas aeruginosa* because of its capability of converting (±)indan-1,2-diol to optically active 2-hydroxy-1-indanone and identified as *Pseudomonas aeruginosa* IN.

Strain 2HI is a gram-positive coryneform and was identified as Corynebacterium.sp.2HI for reasons that it contains mycolic acids mainly consisting of hexadecanoic acid and octadecanoic acid as fatty acids and the amino acid in peptidoglycan of its cell wall is mesodiaminopimelic acid.

Strain 1HE is a gram-positive coryneform and was identified as Arthorobacter.sp.1HE for reasons that it contains iso/antiiso branched acids but no mycolic acids as fatty acids and the amino acid in peptidoglycan of its cell wall is lysine.

Strain 1HB was identified as Arthrobacter.sp.1HB for the same reasons as for 1HE.

The strains described above are deposited at the National Institute of Bioscience and Human-Technology, Agency of Industrial Science and Technology as of Oct. 27, 1995. The deposit numbers are FERM P-15259 for *Bacillus cereus* 2HB, PERM P-15260 for *Pseudomonas aeruginosa* IN, FERM P-15258 for Corynebacterium.sp.2HI, FERM P-15257 for Arthrobacter.sp.1HE, and FERM P-15256 for Arthrobacter.sp.1HB.

The deposit numbers for international deposit based on the Budapest Treaty are FERM BP-5782 for Arthrobacter.sp.1HE and FERM BP-5783 for *Pseudomonas aeruginosa* IN.

The medium to be used for the cultivation of the microbes of this invention may be either liquid or solid, but a liquid medium is appropriate for a large-scale operation. A source of carbon, a source of nitrogen, inorganic substances and nutrients are added in suitable amounts to the medium. Substances useful as the source of carbon are glucose, lactose, sucrose, maltose, dextrin, starch, glycerin, mannitol, and oils and fats while those useful as the source of nitrogen are meat extract, yeast extract, corn steep liquor, peptone, and urea. Useful as inorganic substances are salts containing sodium, potassium, calcium and magnesium and salts of metals such as iron, manganese, zinc, cobalt and nickel. In addition, amino acids, peptides, vitamins and nucleic acids are used as needed. The cultivation is carried out at a pH of 6.0 to 7.0 and at a temperature of 27 to 30° C.

For the action of the aforementioned microbes on the starting material (a), that is, (±)indan-1,2-diol or its 2-formate derivative, given microbes or their cultures are added to the starting material (a) and the mixture is allowed to react at pH 8.0 and 30° C. for 12 to 72 hours. Then, the reaction products are extracted with an organic solvent and processed by silica gel column chromatography to give an optically active indan derivative of high optical purity.

The action of microbes in this manner enables the preparation of optically active 2-hydroxy-1-indanone and/or optically active indan-1,2-diol from (±)indan-1,2-diol or its 2-formate derivative. The principle underlying such action is interpreted as follows. While acting on two enantiomers, (±)- and (−)-forms, of (±)indan-1,2-diol or its 2-formate derivative according to the process of this invention, the aforementioned microbes selectively recognize and oxidize only the enantiomer with its hydroxyl group at the benzyl position of one configuration whether it is cis or trans, and further hydrolyze the 2-formyloxy group in case it is present, to give optically active 2-hydroxy-1-indanone. In consequence, an optically active indan-1,2-diol of the opposite spatial configuration unconcerned in the oxidation is bound to become concentrated. The indan-1,2-diol obtained have the configuration as described above in almost all of the examples to be described later, but there are some exceptions. For example, in the cases where the product is (R)2-hydroxy-1-indanone, almost always optically active indan-1,2-diol with the spatial configuration reversed at 2-position (adjacent to the benzyl group), that is, of (S) form (also represented as 2S), is obtained simultaneously, but on rare occasions indan-1,2-diol of the same (R) form is obtained. This exception may be explained in several ways. One example of such explanation is that an optically active 2-hydroxy-1-indanone produced at high rate, or preferntially, by the aforementioned oxidation decomposes and disappears extremely rapidly by the action of microbes compared with a slow-forming optically active 2-hydroxy-1-indanone of opposite spatial configuration and, as a result, optically active indan-1,2-diol and 2-hydroxy-1-indanone of the same spatial configuration are obtained.

It is possible, in those cases, to obtain only optically active 2-hydroxy-1-indanone and the embodiments of this invention include such cases.

At any rate, the preparation of optically active 2-hydroxy-1-indanone and/or optically active indan-1,2-diol according to the process of this invention is made possible by a large difference in the reaction rate of the aforementioned microbes with (±)indan-1,2-diol or its 2-formate derivative.

Selection of the kind of (±)indan-1,2-diol and microbes enables the preparation of optically active 2-hydroxy-1-indanone and/or optically active indan-1,2-diol and the product is separated or purified in the usual manner and taken as the final product or used as a raw material in the next step.

Where the final target product is cis-1-amino-2-indanol, it is desirable to use 2-hydroxy-1-indanone with an optical purity of 50% e.e. or more, preferably 95% e.e. or more. Higher optical purity leads not only to high yield of the final target product but also to ease of purification. In particular, where the final target product is (1S,2R)-cis-1-amino-2-indanol that is important as intermediate for pharmaceuticals, it is desirable to use (R)2-hydroxy-1-indanone with an optical purity of 50% e.e. or more, preferably 95% e.e. or more.

A compound of the aforementioned general formula (1) can be prepared readily by the following procedure. 2-Hydroxy-1-indanone or its derivative represented by the following general formula (3)

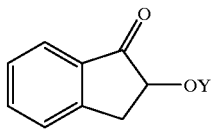

(3)

(wherein Y is hydrogen atom, acyl group or benzyl group) is allowed to react with a hydroxylamine or hydrazine of the following general formula (4) (wherein X and R are as defined earlier) or its salt with a mineral acid such as hydrochloride or sulfate in the presence of a base such as pyridine and sodium hydroxide to effect condensation with elimination of water (see J. March, "Advanced Organic Chemistry," 4th Ed., pp. 904–907, John Wily & Sons, New York, 1992).

Here 2-hydroxy-1-indanone or its derivative represented by the general formula (3) can be prepared easily by a variety of methods including those in the public domain.

For example, the following methods are available: ① The reaction of 1-indanone with bromine gives 2-bromo-1-indanone, which is treated with a carboxylic acid salt such as acetate, formate and benzoate or with the alkoxide of benzyl alcohol and, as desired, further hydrolyzed or debenzylated; ② 1-Indanone or 2-indanone is oxidized by enzymes; ③ Indan-1,2-diol is oxidized by microbes; ④ Indene oxide is oxidized by dimethyl sulfoxide under acidic conditions; ⑤ 1-Indanone is directly hydroxylated at 2-position; ⑥ 3-Phenyl-2-hydroxypropionic acid or its derivative is cyclized. Of the methods described above, the oxidation by enzymes or microbes is capable of yielding optically active 2-hydroxy-1-indanone and is used advantageously for the preparation of this optically active compound as target product for further use as intermediate for pharmaceuticals.

As for hydroxylamines or hydrazines represented by the general formula (4), the hydroxylamines include hydroxylamine, o-benzylhydroxylamine and o-methylhydroxylamine and they are normally used as their hydrochlorides or sulfates. Moreover, it is possible to use a hydroxylamine derivative which plays the same role as hydroxylamine in the aforementioned dehydrating condensation reaction, for example, hydroxylamine-o-sulfonic acid. Of these compounds, hydroxylamine is preferable as it is commercially produced on a large scale and available at low cost. The hydrazines include hydrazine, methylhydrazine, phenylhydrazine and benzylhydrazine.

Compounds of the general formula (1) of this invention have two geometrical isomers, namely E and Z forms, in respect to =N—X—R and either of them may be used. Furthermore, there exist optical isomers as the carbon atom at 2-position is asymmetric and they can be used satisfactorily.

The reaction of a compound of the general formula (1) with hydrogen or a hydrogen donor in the presence of a heterogeneous hydrogenation catalyst gives cis-1-amino-2-indanol. A hydrogen donor here refers to a compound which generates hydrogen under the reaction conditions such as tetralin, decalin and formic acid. The amount of such hydrogen donor, when used singly, is preferably in excess of the compound of the general formula (1). With the use of hydrogen, the pressure is usually from normal to 100 atmospheric pressure although it varies with the amount of catalyst and the reaction temperature, and the reaction proceeds at normal pressure to 30 atmospheric pressure in most cases.

Heterogeneous hydrogenation catalysts useful here are those which are used in the ordinary catalytic hydrogenation and include, as will be described later, catalysts based on nickel, palladium or platinum, those based on cobalt such as Raney cobalt, reduced cobalt and Urushibara cobalt, those based on copper chromate, those based on ruthenium such as ruthenium oxide and ruthenium/carbon, and those based on rhodium such as rhodium/alumina and rhodium/carbon.

The aforementioned heterogeneous hydrogenation catalyst works as follows in the reaction of this invention. A heterogeneous hydrogenation catalyst on whose surface hydrogen is adsorbed attacks the double bond C=N in a compound of the general formula (1) to effect cis addition of two hydrogen atoms. During this attack, the adjacent oxy group (—OY) hinders the addition reaction because of its bulkiness and the catalyst attacks the C=N double bond from the side opposite to the oxy group. As the result, the amino group (—NH₂) and the oxy group (—OY) are positioned cis to each other and a compound represented by the general formula (2) is selectively produced. Examples of heterogeneous hydrogenation catalysts which work markedly in this manner are those based on nickel, palladium or platinum, perferably thosed based on palladium.

The nickel-based catalysts here include Raney nickel, sponge nickel, Urushibara nickel, reduced nickel and nickel/kieselguhr and they are used usually in an amount 0.01 to 10 times, preferably 0.1 to 5 times, that of a compound of the general formula (1) on a weight basis. With the use of less than 0.01 times of the catalyst, the reaction proceeds so slowly that side reactions become predominant. On the other ha the use of more than 10 times of the catalyst does not improve the reaction to any significant degree and is not economical. The nickel-based catalyst is normally used as a suspension in a protic solvent such as ethanol and methanol and it is preferable to add to the suspension a basic substance such as ammonia, sodium hydroxide, potassium hydroxide, potassium carbonate and sodium methoxide in an amount 1 to 10 times that of the compound of the general formula (1) on a mole basis.

The palladium-based catalysts include fine metallic palladium particles (the so-called palladium black), fine metallic palladium particles supported on a carrier such as activated carbon, alumina and barium sulfate (for example, palladium/carbon, palladium/alumina and Pd/BaSO₄), and palladium oxide. The amount of the palladium-based catalyst varies with the content of palladium, but it is normally 0.01 to 5 times, preferrably 0.05 to 2 times, that of a compound of the general formula (1) on a weight basis in the case of 5%Pd/C. These palladium-based catalysts allow the use of a wide variety of organic solvents in the reaction and, in particular, a neutral or acidic solvent such as methanol, ethanol, acetic acid and ethyl acetate may be used advantageously. It is also preferable to add to the aforementioned solvents an acidic compound such as hydrogen chloride, hydrogen bromide and sulfuric acid in an amount 1 to 10 times that of a compound of the general formula (1) on a mole basis.

The platinum-based catalysts include platinum oxide, fine platinum particles (the so-called platinum black), and fine platinum particles supported on a carrier such as activated carbon (the so-called platinum/carbon) and the amount to be used and the reaction solvent are the same as in the case of the palladium-based catalysts.

The reaction of a compound of the general formula (1) and hydrogen or a hydrogen donor in the presence of a heterogeneous hydrogenation catalyst is carried out in the temperature range from −10 to 200° C., preferably from 0 to 150° C., more preferably from 10 to 100° C.

It is possible in this manner to prepare cis-1-amino-2-indanol or its derivative represented by the general formula (2), and when Y in the resulting derivative of the general formula (2) is acyl or benzyl group, the derivative in question can be converted easily to the target product cis-1-amino-2-indanol by removing the acyl group by hydrolysis or the benzyl group by hydrogenolysis. This product can also be isolated as a hydrochloride.

Now, the aforementioned hydrogenolysis may be carried out simultaneously while effecting the process of this invention with the use of a compound of the general formula (1) and this enables the preparation of cis-1-amino-2-indanol in one step.

According to one mode of the process of this invention, it is possible to prepare optically active cis-1-amino-2-indanol of high optical purity, useful as synthetic intermediate for pharmaceuticals, on a commercial scale at low cost.

According to another mode of the process of this invention, it is possible to prepare optically active 2-hydroxy-1-indanone or indan-1,2-diol of high optical purity and use the compound thus obtained to prepare at low cost optically active synthetic intermediates useful particularly for pharmaceuticals.

According to a still another mode of the process of this invention, it is possible to prepare 2-indanol derivatives, specifically cis-1-amino-2-indanol or its derivatives, readily at low cost.

PREFERRED EMBODIMENTS OF THE INVENTION

The process of this invention will be described in detail below with reference to the accompanying examples.

In the following examples, the optical purity was determined, unless otherwise specified, by extracting the reaction products with an organic solvent and applying high-performance liquid chromatography with the use of an optical resolution column [column, CHIRACEL OB or OJ (4.6 mm ID×250 mm) manufactured by Daicel Chemical Industries, Ltd.; mobile phase, hexane/2-propanol=9/1; detection, 254 mm; flow rate, 0.5 ml/minute).

[Retention time: (R)2-hydroxy-1-indanone, 17 minutes (Column OB); (S)-2-hydroxy-1-indanone, 23 minutes (Column OB); (1R,2S)-cis-indan-1,2-diol, 14.6 minutes (Column OJ); (1S,2R)-cis-indan-1,2-diol, 18.4 minutes (Column OJ); (1R,2R)-trans-indan-1,2-diol, 14.2 minutes (Column OJ); (1S,2S)-trans-indan-1,2-diol, 12.8 minutes (Column OJ)].

The yield was determined by high-performance liquid chromatography with the use of a reversed-phase column [column, ODS-80Ts (4.6 mm ID×150 mm) manufactured by Tosoh Corporation; mobile phase, water/acetonitrile=7/3; detection, 254 mm; flow rate, 0.5 ml/minute]. [Retention time: 2-hydroxy-1-indanone, 9 minutes; cis-indan-1,2-diol, 6.5 minutes; trans-indan-1,2-diol, 5.8 minutes].

EXAMPLES 1–5

In a 500-ml Erlenmeyer flask with baffle was placed 50 ml of the TPU-1 medium containing 0.1% of 1-hydroxyindan (0.1%), the medium was sterilized, a platinum loopful of each of the strains shown in Table 1 was inoculated onto the medium and cultivated in a gyrotary shaker at 230 rpm for 96 hours. Upon completion of the cultivation, the microbes were separated by centrifugation and washed once with physiological saline to obtain the live microbes. The live microbes suspended in 1 ml of a reaction solution containing $K_2HPO_4$ (1.7 g/l), $MgSO_4.7H_2O$ (1.5 g/l) and $FeSO_4.7H_2O$ (0.05 g/l) at pH 8.0 were placed a stoppered 15×180 mm test tube, 20 mg of (±)cis-indan-1,2-diol and 1 ml of hexadecane were added, and the mixture was shaken and allowed to react for a specified length of time at 30° C. After completion of the reaction, the hexadecane was removed by extraction with 2 ml of n-octane, and the reaction product was extracted twice with 2 ml of ethyl acetate. The ethyl acetate layer was dried over anhydrous sodium sulfate, concentrated, and submitted to high-performance liquid chromatography to determine the quantity and optical purity of the product 2-hydroxy-1-indanone and the remaining cis-indan-1,2-diol.

Here, the TPU-1 medium contains $K_2HPO_4$ (2 g/l), NaCl (1 g/l), $MgSO_4.7H_2O$ (0.2 g/l), yeast extract (0.5 g/l), ammonium sulfate (2 g/l), a solution of trace elements (10 ml/l), and a mixture of vitamins (10 ml/l) at pH 7.0. The solution of trace elements contains Titrplex IV (0.5 g/l), $FeSO_4.7H_2O$ (0.2 g/l), $ZnSO_4.7H_2O$ (0.01 g/l), $MnCl_2.4H_2O$ (0.003 g/l), $H_3BO_4$ (0.03 g/l), $CoCl_2.6H_2O$ (0.02 g/l), $CuCl_2.2H_2O$ (0.001 g/l), $NiCl_2.6H_2O$ (0.002 g/l) and $Na_2MoO_4.2H_2O$ (0.003 g/l). The mixture of vitamins contains biotin (20 μg/l), calcium pantothenate (4 mg/l), thiamine hydrochloride (4 mg/l), inositol (20 mg/l), pyridoxine hydrochloride (4 mg/l), nicotinic acid (4 mg/l), p-aminobenzoic acid (2 mg/l), riboflavine (2 mg/l) and folic acid (100 μg/l).

The results obtained are shown in Table 2.

EXAMPLES 1–5

The same reactant composition as in Example 1 prepared from the live microbes obtained by cultivating as in Example 1 was shaken with 20 mg of the substrate (±)trans-indan-1,2-diol at 30° C and allowed to react for a specified length of time. Upon completion of the reaction, the reaction mixture was extracted and submitted to the determination by high-performance liquid chromatography of the amount and optical purity of the product 2-hydroxy-1-indanone and the remaining trans-indan-1,2-diol.

The results obtained are shown in Table 3.

EXAMPLE 11

Microbes were cultivated by inoculating Arthrobacter.sp.1HB into 10 ml of a medium containing on a weight basis 0.2 % of $K_2HPO_4$, 0.1% of NaCl, 0.02% of $MgSO_4 \cdot 7H_2O$, 1.5% of sodium gluconate, 0.7% of yeast extract and 0.05% of 1-hydroxyindan at pH 7.0 and shaking at 30° C. for 48 hours. The microbes were collected by centrifugation, suspended in 1 ml of a reactant solution containing 10 mM of $K_2HPO_4$, 6 mM of $MgSO_4 \cdot 7H_2O$ and 0.16 mM of $FeSO_4 \cdot 7H_2O$ at pH 8.0, mixed with 37.5 mg (final concentration 250 mM) of the substrate (±)cis-indan-1,2-diol and shaken at 30° C. for 2 hours. Upon completion of the reaction, the ethyl acetate extract of the reaction mixture was analyzed by high-performance liquid chromatography to confirm the formation of (R)2-hydroxy-1-indanone of 60% e.e. in 43.6% yield and the recovery of (1R,2S)-cis-indan-1,2-diol of 13.8% e.e. in 25.6% yield.

EXAMPLE 12

A mixture of 1 ml of a suspension of the microbes of Arthrobacter.sp.1HB strain prepared as in Example 11 and 37.5 mg (final concentration 250 mM) of (±)trans-indan-1,2-diol was allowed to react in the same manner and the results confirmed the formation of (S)2-hydroxy-1-indanone of 52% e.e. in 13.4% yield and the recovery of (1R,2R)-trans-indan-1,2-diol of 21.6% e.e. in 55.8% yield.

EXAMPLE 13

Microbes were cultivated by inoculating Arthrobacter.sp.1HE into 10 ml of a medium containing on a weight basis 0.2% of $K_2HPO_4$, 0.1% of NaCl, 0.02% of $MgSO_4 \cdot 7H_2O$, 0.25% of corn steep liquor and 0.05% of 1-hydroxyindan at pH 7.0 and shaking at 30° C. for 48 hours. A suspension of the microbes was prepared as in Example 11, mixed with 15 mg (final concentration 100 mM) of (±)cis-indan-1,2-diol, and the reaction was effected in the same manner to confirmed the formation of (R)2-hydroxy-1-indanone of 99.9% e.e. or more in 30.0% yield and the recovery of (1R,2S)-cis-indan-1,2-diol of 65.2% e.e. in 10.3% yield.

EXAMPLE 14

A mixture of 1 ml of a suspension of the microbes of Arthrobacter.sp.1HE strain prepared as in Example 13 and 15 mg (final concentration 100 mM) of (±)trans-indan-1,2-diol was allowed to react in the same manner and the results confirmed the formation of (S)2-hydroxy-1-indanone of 39.5% e.e. in 3.5% yield and the recovery of (1R,2R)-trans-indan-1,2-diol of 65.2% e.e. in 70.1% yield.

EXAMPLE 15

Microbes were cultivated by inoculating Pseudomonas aeruginosa IN into 10 ml of a medium containing on a weight basis 0.2% of $K_2HPO_4$, 0.1% of NaCl, 0.02% of $MgSO_4 \cdot 7H_2O$, 0.6% of yeast extract and 0.05% of 1-hydroxyindan at pH 7.0 and shaking at 30° C. for 48 hours. A suspension of the microbes was prepared as in Example 11, mixed with 15 mg (final concentration 100 mM) of (±)cis-indan-1,2-diol, and the reaction was effected in the same manner to confirm the formation of (R)2-hydroxy-1-indanone of 99.9% e.e. or more in 13.2% yield and the recovery of (1R,2S)-cis-indan-1,2-diol of 5.8% e.e. in 57.3% yield.

EXAMPLE 16

A mixture of 1 ml of a suspension of the microbes of Pseudomonas aeruginosa IN strain prepared as in Example 15 and 15 mg (final concentration 100 mM) of (±)trans-indan-1,2-diol was allowed to react in the same manner and the results confirmed the formation of (R)2-hydroxy-1-indanone of 97.5% e.e. in 34.3% yield and the recovery of (1S,2S)-trans-indan-1,2-diol of 50.2% e.e. in 30.5% yield.

The results of Examples 11 to 16 are shown in Table 4.

EXAMPLE 17

A mixture of 1 ml of a suspension of the microbes of Arthrobacter.sp1HB strain prepared as in Example 11 and 8.9 mg (final concentration 50 mM) of (±)cis-indan-1,2-diol-2-formate was allowed to react for 7 hours and the results indicated the formation of (R)2-hydroxy-1-indanone of 79.4% e.e. in 13.4% yield.

EXAMPLE 18

A mixture of 1 ml of a suspension of the microbes of Arthrobacter.sp1HE strain prepared as in Example 13 and 8.9 mg (final concentration 50 mM) of (±)cis-indan-1,2-diol-2-formate was allowed to react for 7 hours and the results indicated the formation of (R)2-hydroxy-1-indanone of 78.2% e.e. in 13.3% yield.

EXAMPLE 19

A mixture of 1 ml of a suspension of the microbes of Pseudomonas aeruginosa IN strain prepared as in Example 15 and 8.9 mg (final concentration 50 mM) of (±)cis-indan-1,2-diol-2-formate was allowed to react for 7 hours and the results indicated the formation of (R)2-hydroxy-1-indanone of 46.0% e.e. in 3.5% yield.

The results of Examples 17–19 are shown in Table 5.

TABLE 2

| Example No. | Strain | Reaction time (hr) | 2-Hydroxy-1-indanone | | | cis-Indan-1,2-diol | | |
|---|---|---|---|---|---|---|---|---|
| | | | Yield (%) | Configuration | Optical purity (% e.e.) | Yield % | Configuration | Optical purity (% e.e.) |
| 1 | Arthrobacter · sp. 1HB | 72 | 19.8 | (S) | 11.8 | 28.7 | (1R, 2S) | 31.3 |
| 2 | Arthrobacter · sp. 1HE | 72 | 6.10 | (R) | 45.0 | 44.8 | (1R, 2S) | 30.7 |
| 3 | Bacillus cereus 2HB | 12 | 9.85 | (R) | 87.4 | 42.8 | (1R, 2S) | 83.2 |
| 4 | Corynebacteriun · sp. 2HI | 12 | 12.2 | (R) | 85.8 | 54.4 | (1R, 2S) | 86.5 |
| 5 | Pseudomonas aeruginosa IN | 24 | 0.97 | (S) | 60.6 | 62.4 | (1S, 2R) | 6.2 |

TABLE 3

| Example No. | Strain | Reaction time (hr) | 2-Hydroxy-1-indanone | | | cis-Indan-1,2-diol | | |
|---|---|---|---|---|---|---|---|---|
| | | | Yield (%) | Configuration | Optical purity (% e.e.) | Yield % | Configuration | Optical purity (% e.e.) |
| 6 | Arthrobacter · sp. 1HB | 72 | 10.0 | (R) | 36.8 | 32.7 | (1R, 2S) | 7.8 |
| 7 | Arthrobacter · sp. 1HE | 72 | 1.82 | (R) | 5.2 | 43.2 | (1S, 2S) | 35.2 |
| 8 | *Bacillus cereus* 2HB | 72 | 1.20 | (S) | 90.4 | 39.4 | (1R, 2R) | 27.0 |
| 9 | Corynebacteriun · sp. 2HI | 72 | 2.90 | (R) | 5.6 | 41.0 | (1R, 2R) | 13.8 |
| 10 | *Pseudomonas aeruginosa* IN | 24 | 2.60 | (R) | >99.9 | 41.2 | (1S, 2S) | 82.2 |

TABLE 4

| Example No. | Strain | Reaction time (hr) | Substrate concentration (mM) | 2-Hydroxy-1-indanone | | | | | |
|---|---|---|---|---|---|---|---|---|---|
| | | | | Yield (%) | Configuration | Optical purity (% e.e.) | Yield (%) | Configuration | Optical purity (% e.e.) |
| | | | | | | | cis-Indan-1,2-diol | | |
| 11 | Arthrobacter.sp. 1HB | 2 | 250 | 43.6 | (R) | 60.0 | 25.6 | (1R, 2S) | 13.8 |
| 12 | Arthrobacter.sp. 1HE | 2 | 100 | 30.0 | (R) | >99.9 | 10.3 | (1R, 2S) | 65.2 |
| 13 | Pseudomonas aeruginosa IN | 2 | 100 | 13.2 | (R) | >99.9 | 57.3 | (1R, 2S) | 5.8 |
| | | | | | | | trans-Indan-1,2-diol | | |
| 14 | Arthrobacter.sp. 1HB | 2 | 250 | 13.4 | (R) | 52.0 | 55.8 | (1R, 2R) | 21.6 |
| 15 | Arhtorbacter.sp. 1HE | 2 | 100 | 3.5 | (S) | 39.5 | 70.1 | (1R, 2R) | 65.2 |
| 16 | Pseudomonas aeruginosa IN | 2 | 100 | 34.3 | (R) | 97.5 | 30.5 | (1S, 2S) | 50.2 |

TABLE 5

| Example No. | Strain | Reaction time (hr) | Substrate concentration (mM) | 2-Hydroxy-1-indanone | | |
|---|---|---|---|---|---|---|
| | | | | Yield (%) | Configuration | Optical purity (% e.e.) |
| 17 | Arthrobacter · sp. 1HB | 7 | 50 | 13.4 | (R) | 79.4 |
| 18 | Arthrobacter · sp. 1HE | 7 | 50 | 13.3 | (R) | 78.2 |
| 19 | *Pseudomonas aeruginosa* IN | 7 | 50 | 3.5 | (R) | 46.0 |

EXAMPLE 20

The microbes of Arthrobacter.sp.1HE cultivated in 25 l of a medium of the same composition as in Example 13 were washed, suspended in 1.25 l of a reactant solution of the same composition as in Example 13, mixed with 13.5 g (final concentration 72 mM) of the substrate (±)cis-indan-1,2-diol and shaken at 30° C. for 24 hours. Upon completion of the reaction, the reaction mixture was extracted with ethyl acetate and purified by silica gel column chromatography (solvent; hexane/ethyl acetate=3/2) to give 1.31 g (12.3% yield) of (R)2-hydroxy-1-indanone of 99.9% e.e. or more as colorless plate crystals.

The results of NMR analysis were as follows:

$^1$H-NMR (CDCl$_3$) dppm: 7.762 (d, 1H, J=7.8 Hz), 7.637 (t, 1H, J=7.5 Hz), 7.459 (dd, 1H, J=0. 8, 7.5 Hz), 7.401 (t, 1H, J=7.6 Hz), 4.569 (t, 1H, J=5.8 Hz), 3.583 (dd, 1H, J=8.0, 16.5 Hz), 3.450 (br, 1H), 3.026 (dd, 1H, J=5.1, 16.5 Hz)

$^{13}$C-NMR (CDCl$_3$) dppm: 206.64, 150.97, 135.89, 134.08, 128.03, 126.81, 124.46, 74.28, 35.17.

Supplementary Example 1
Synthesis of 2-hydroxy-1-indanone oxime

In 30 ml of pyridine was dissolved 2.56 g (17.3 mmol) of 2-hydroxy-1-indanone, the solution was cooled to 0° C. and 1.92 g (28.5 mmol) of hydroxylamine hydrochloride was added. The mixture was stirred at 0° C. for 3 hours, the pyridine was removed under reduced pressure, the residue was dissolved in methylene chloride, the solution was washed respectively with a 1:1 mixture of a 10% aqueous solution of citric acid and a saturated aqueous solution of sodium chloride and with a saturated aqueous solution of sodium chloride, and the organic layer was dried over anhydrous sodium sulfate and concentrated in a rotary evaporator to give a solid.

The solid thus obtained was purified by silica gel column chromatography to give two geometrical isomers A and B of 2-hydroxy-1-indanone oxime in white crystals, 1.08 g of A in 38% yield and 707 mg of B in 25% yield.

Geometrical isomer A of 2-hydroxy-1-indanone oxime was analyzed by $^1$H-NMR, MS and IR to yield the following results.

$^1$H-NMR (200 MHz, CDCl$_3$): δ 3.02 (dd, J=7.9, 17.4 Hz, 1H), 3.46 (dd, J=7.1, 17.4 Hz, 1H), 3.61 (s, br, 1H), 5.44 (dd, J=3.5, 7.9 Hz, 1H), 7.33 (m, 3H), 7.61 (d, J=7.5 Hz, 1H), 8.63 (s, br, 1H).

MS (ESI, neg.) m/z=162.1 (found), 162.1 (calcd. for M$^-$−1).

IR (KBr): 3511, 3248, 3104, 2909, 1489, 1461, 1318, 1090, 1032, 934, 754, 718 cm$^{-1}$.

Geometrical isomer B of 2-hydroxy-1-indanone oxime was analyzed by $^1$H-NMR, MS and IR in the same manner to yield the following results.

$^1$H-NMR (200 MHz, CDCl$_3$): δ 3.02 (dd, J=7.1, 16.8 Hz, 1H), 3.43 (dd, J=7.1, 16.8 Hz, 1H), 5.01 (dd, J=3.8, 7.5 Hz, 1H), 7.35 (m, 3H), 8.32 (d, J=7.3 Hz, 1H).

MS (ESI, neg.) m/z=162.1 (found), 162.1 (calcd. for M$^-$−1).

IR (KBr): 3209, 3070, 2932, 1657, 1483, 1462, 1416, 1310, 1046, 1013, 974, 743 cm$^{-1}$.

Supplementary Example 2
Synthesis of (R)2-hydroxy-1-indanone oxime

In 23 ml of pyridine was dissolved 2.00 g (13.5 mmol) of (R)2-hydroxy-1-indanone of optical purity 99.9% e.e. or more prepared in the same manner as in Example 20, the solution was cooled to −15° C., and 1.30 g (20.3 mmol) of hydroxylamine hydrochloride was added. The mixture was stirred at −15° C. for 1 hour, at 0° C. for 2 hours and at room temperature for 12 hours, the pyridine was removed under reduced pressure, the residue was dissolved in methyl acetate, the solution was washed respectively with a 1:1 mixture of a 10% aqueous solution of citric acid and a saturated aqueous solution of sodium chloride and with a saturated aqueous solution of sodium chloride, and the organic layer was dried over anhydrous sodium sulfate and concentrated in a rotary evaporator to give a solid. The solid was recrystallized from a mixture of hexane and methyl acetate to give 1.67 g (75.6% yield) of a mixture of two geometrical isomers A and B of (R)2-hydroxy-1-indanone oxime in white crystals. Analysis of th e mixture by MS yielded the following results:

MS (ESI, neg.) m/z=162.2 (found), 163.1 (calcd. for M$^-$−1).

It was confirmed by high-performance liquid chromatography [Daicel Chemical Industries' CHIRACEL AD with hexane/2-propanol (0.4/0.1) and CHIRACEL OB with hexane/2-propanol (0.6/0.1)] that the two geometrical isomers A and B of (R)2-hydroxy-1-indanone oxime were present at a ratio of 35:65 and both showed an optical purity (e.e.) of 99% or more.

EXAMPLE 21

Into a 200-ml eggplant-shaped flask were introduced 930 mg (5.70 mmol) of the geometrical isomer B of 2-hydroxy-1-indanone oxime prepared in Supplementary Example 1 and 210 mg of palladium black and the flask was filled with hydrogen gas by replacing air three times with hydrogen gas. To the flask were added 80 ml of methanol and 9.28 ml of a methanolic solution of hydrogen chloride with a normality of 1.78, and the mixture was stirred under a hydrogen atmosphere of normal pressure at room temperature for 26 hours.

Upon completion of the reaction, the insoluble matters were separated by filtration and washed with 300 ml of hot methanol. The filtrate and the washings were combined, concentrated under reduced pressure, the solid obtained was dissolved in 200 ml of ethyl acetate, and the solution was washed twice with 50 ml of an aqueous solution saturated with potassium carbonate and sodium chloride and once with 50 ml of a saturated aqueous solution of sodium chloride.

The washed solution was dried over anhydrous sodium sulfate and concentrated under reduced pressure to give 531 mg (62% yield) of white solid of 1-amino-2-indanol.

The solid thus obtained was found by high-performance liquid chromatography [ODS, acetonitrile/0.1% aqueous TFA (1/9)] to be a mixture of cis and trans isomers at the cis/trans ratio of 95.5:4.5 [rate of eluation, 1 ml/minute; retention time, 6.67 minutes (trans) and 7.45 minutes (cis)].

The cis and trans isomers were fractionated by high-performance liquid chromatography (under the same conditions as above) and isolated. The procedure established for the determination of cis or trans was followed and the compound which reacts with triphosgene to form oxazolidone was identified as cis-1-amino-2-indanol.

Analyses of cis-1-amino-2-indanol by $^1$H-NMR, $^{13}$C-NMR, MS and IR yielded the following results.

$^1$H-NMR (200 MHz, CD$_3$OD): δ 2.87 (dd, J=3.2, 16.1 Hz, 1H), 3.05 (dd, J=5.3, 16.1 Hz, 1H), 4.13 (d, J=5.1 Hz, 1H), 4.39 (m, 1H), 7.17 (m, 3H), 7.38 (m, 1H).

$^{13}$C-NMR (50.3 MHz, CD$_3$OD): δ 40.0, 60.4, 75.2, 125.3, 126.0, 127.8, 128.6, 141.8, 145.1.

MS (ESI, pos.) m/z=149.8 (found), 149.1 (calcd. for MH$^+$).

IR (KBr): 3345, 3274, 3080, 2957, 2920, 1723, 1708, 1678, 1476, 1454, 1377, 1337, 1264, 1049, 997, 908 cm$^{-1}$.

Moreover, analyses of trans-1-amino-2-indanol by $^1$H-NMR, $^{13}$C-NMR, MS and IR yielded the following results.

$^1$H-NMR (200 MHz, CD$_3$OD): δ 2.76~2.88 (m, 1H), 3.23~3.34 (m, 1H), 4.25~4.33 (m, 2H), 7.23~7.30 (m, 3H), 7.37~7.42 (m, 1H).

$^{13}$C-NMR (50.3 MHz, CD$_3$OD): δ 39.9, 64.0, 80.0, 125.0, 126.2, 128.3, 129.8, 140.9, 141.4 MS (ESI, pos.) m/z=149.8 (found), 150.1 (calcd. for MH$^+$).

The conversion of cis-1-amino-2-indanol to the corresponding oxazolidone was carried out as follows.

In 40 ml of ethyl acetate was dissolved 5 mg (0.358 mmol) of the 1-amino-2-indanol obtained at retention time 7.45 minutes in the aforementioned high-performance liquid chromatography, 53.67 μl (0.377 mmol) of triethylamine and 37.3 mg (0.123 mmol) of triphosgene were added to the solution, and the mixture was stirred at room temperature for 6 hours. The crystals separated were filtered off and the filtrate was washed twice with an aqueous solution saturated with sodium carbonate and sodium chloride, then washed once with a saturated aqueous solution of sodium chloride, dried over anhydrous sodium sulfate, and concentrated under reduced pressure.

The resulting solid was dissolved in methylene chloride, hexane was added to the solution and the crystals precipitated were filtered and washed with hexane to give 48.2 mg (77% yield) of oxazolidone in white crystals.

The oxazolidone thus obtained was analyzed by $^1$NMR, $^{13}$C-NMR, MS and IR to yield the following results.

$^1$H-NMR (200 MHz, CDCl$_3$): δ 3.37 (m, 2H), 5.16 (dd, J=0.66, 8.0 Hz, 1H), 5.41 (m, 1H), 6.09 (s, br, 1H), 7.30 (m, 4H).

$^{13}$C-NMR (50.3 MHz, CD$_3$OD): δ 38.9, 61.1, 80.6, 124.6, 125.7, 127.9, 129.5, 139.8, 140.2, 159.2.

MS (ESI, pos.) m/z=229.9 (found), 230.1 (calcd. for M+Na$^+$+MeOH).

IR (KBr): 3260, 1754, 1709, 1485, 1458, 1395, 1331, 1233, 1204, 1183, 1107, 963, 752 cm$^{-1}$.

EXAMPLES 22 AND 23

1-Amino-2-indanol was synthesized as in the aforementioned Example 21 except using 223 mg of 5% palladium/ carbon in Example 22 and 233 mg of 5% palladium/alumina in Example 23 as catalyst in place of the palladium black.

In Example 22 where 223 mg of 5% palladium/carbon was used, 1-amino-2-indanol was obtained in 95% yield at the cis/trans ratio of 84/16.

In Example 23 where 233 mg of 5% palladium/alumina was used, 1-amino-2-indanol was obtained in 96% yield at the cis/trans ratio of 92/8.

EXAMPLE 24

In a 300-ml eggplant-shaped flask were placed 1.00 g (6.13 mmol) of a 35:65 mixture of the geometrical isomers A and B of (R)2-hydroxy-1-indanone prepared in Supplementary Example 2 and 50 mg of palladium black and the flask was filled with hydrogen gas by replacing air three times with hydrogen gas. To the flask were added 250 ml of methanol and 3.13 g of a 47.5% aqueous solution of hydrobromic acid and the mixture was stirred under a hydrogen atmosphere of normal pressure at room temperature for 20 hours. Upon completion of the reaction, the insoluble matters were separated by filtration and washed with 300 ml of hot methanol. The filtrate and the washings were combined and concentrated under reduced pressure and the resulting solid was dissolved in 200 ml of ethyl acetate, washed twice with 50 ml of an aqueous solution saturated with sodium carbonate and sodium chloride, then washed once with a saturated aqueous solution of sodium chloride. The washed solution was dried over anhydrous sodium sulfate and concentrated under reduced pressure to yield 821 mg of a white solid. The solid product was analyzed by high-performance liquid chromatography (ODS, methanol:0.2% aqueous phosphoric acid=1:9). The optical purity (e.e.) was determined by converting the product to oxazolidone and analyzing by high-performance liquid chromatography. The results indicate the formation of 1-amino-2-indanol in 90% yield at the cis: trans ratio of 95.6:4.4. Also, the oxazolidone synthesized from cis-1-amino-2-indanol was 100% in the (1S,2R) form and its antipode, the (1R,2S) form, was not observed.

Analysis by high-performance liquid chromatography: (1) ODS column, mobile phase methanol:0.2% aqueous phosphoric acid=1:9, 1 ml/minute, retention time 4.77 minutes (trans) and 5.34 minutes (cis); (2) daicel Chemical Industries' CHIRACEL OB, mobile phase hexane:ethanol=4:1, 0.5 ml/minute, retention time 23.7 minutes (1R,2s).

EXAMPLES 25–29

The reaction was carried out on the same amount of 2-hydroxy-1-indanone oxime in the same solvent as in example 21 while substituting the palladium black for 233 mg of each of palladium oxide, palladium hydroxide, palladium/asbestos, platinum (IV) oxide, and rhodium/alumina as catalyst.

The kind of catalyst, yield, and cis:trans ratio are shown in table 6.

TABLE 6

| Example No. | Kind of catalyst | Yield (%) | cis:trans ratio |
|---|---|---|---|
| 25 | Palladium oxide | 93 | 88:12 |
| 26 | Palladium hydroxide | 98 | 85:15 |
| 27 | 10% Palladium/asbestos | 88 | 88:12 |
| 28 | Platnum (IV) oxide | 86 | 88:12 |
| 29 | 5% Rhodium/alumina | 5 | 64:37 |

What is claimed is:

1. A process for preparing cis-1-amino-2-indanol or its derivative represented by the following general formula (2):

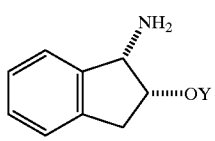

(2)

wherein Y is a hydrogen atom, an acyl group or a benzyl group, which process comprises:

treating 2-hydroxy-1-indanone or its derivative represented by the following general formula (3):

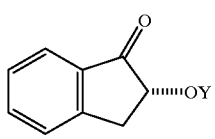

(3)

wherein Y is a hydrogen atom, an acyl group or a benzyl group, with a compound of the following general formula (4):

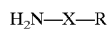

$H_2N$—X—R (4)

wherein X is —O— or —NH—, and R is a hydrogen atom, an alkyl group or an aryl group, to give a compound of the following general formula (1):

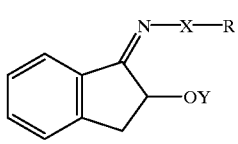

(1)

wherein X is —O— or —NH—, R is a hydrogen atom, an alkyl group, or an aryl group, and Y is a hydrogen atom, an acyl group or a benzyl group; and treating said compound of general formula (1) with hydrogen or a hydrogen donor in the presence of a heterogeneous hydrogenation catalyst and an acidic compound.

2. The process for preparing cis-1-amino-2-indanol or its derivative according to claim 1, wherein in the compound of formula (1), X is —O— and R is a hydrogen atom.

3. The process for preparing cis-1-amino-2-indanol or its derivative according to claim 1, wherein said heterogeneous hydrogenation catalyst is a catalyst based on nickel, palladium or platinum.

4. The process for preparing cis-1-amino-2-indanol or its derivative according to claim 1, wherein said acidic compound is one or more compounds selected from the group consisting of hydrogen chloride, hydrogen bromine and sulfuric acid.

5. The process for preparing cis-1-amino-2-indanol or its derivative according to claim 1, wherein said acidic compound is present in an amount of 1 to 10 times that of the compound according to general formula (1) on a mole basis.

* * * * *